US006423853B1

(12) United States Patent
Moran, Jr. et al.

(10) Patent No.: US 6,423,853 B1
(45) Date of Patent: Jul. 23, 2002

(54) CONTINUOUS OZONOLYSIS OF CYCLOALKENES INTO OZONIDES

(75) Inventors: Edward F. Moran, Jr., Gibbstown, NJ (US); Chester Arthur Thayer, II, Wilmington, DE (US)

(73) Assignee: E. I. du Pont de Nemours & Comp., Wilmington, DE (US)

( * ) Notice: Subject to any disclaimer, the term of this patent is extended or adjusted under 35 U.S.C. 154(b) by 0 days.

(21) Appl. No.: 09/961,427

(22) Filed: Sep. 24, 2001

(51) Int. Cl.[7] .............................................. C07D 301/03

(52) U.S. Cl. ........................ 549/523; 549/513; 549/524; 549/547

(58) Field of Search ................................. 549/512, 513, 549/524, 523, 547

(56) References Cited

U.S. PATENT DOCUMENTS 3,280,183 A    10/1966    Magglio

*Primary Examiner*—Sreenivasan Padmanabhan

(57) ABSTRACT

Continuous processes for converting cycloalkenes into ozonides in which ozone is reacted with a cycloalkene to form an ozonide solution. A portion of the solution is recycled back to the reaction, and additional cycloalkene is provided.

2 Claims, 2 Drawing Sheets

CONTINUOUS OZONOLYSIS OF CYCLOALKENES INTO OZONIDES

BACKGROUND

U.S. Pat. No. 3,280,183, granted Oct. 18, 1966 to Maggiolo, discloses a method of producing a, dicarboxylic acids from eight to twelve carbon atom cycloalkenes. This method begins with a cycloalkene having the same number of carbon atoms as the dicarboxylic acid. The method is said to allow these acids to be produced economically.

There are two steps to the method. First, the cycloalkene is dissolved in a solvent at a concentration "at least about" 10% (the solubility depends on the particular cycloalkene and solvent; a solubility of 20% is disclosed for cyclooctene in isobutyric acid). The solvent is a monobasic acid such as acetic acid, propionic acid, isobutyric acid, etc. The resulting mixture is contacted with a gas containing 2 to 7% ozone at a temperature of 25° C. or less for up to several hours until the cycloalkene is totally reacted to ozonide (ozonolysis). Lower temperature ozonolysis is preferred for economic reasons. When the ozonolysis is complete, the temperature is raised to the range of 65 to 110° C., and the mixture is contacted with an oxygen-containing gas (oxidation). After a period of 1.5 to 13 hours under these conditions, the reaction is complete. Following the oxidation, the product, $\alpha,\omega$ dicarboxylic acid, is purified by vacuum distillation.

Both the temperature of ozonolysis and the conditions for oxidation have a direct effect on the ultimate yield in the conversion of the cycloalkene into $\alpha, \omega$ dicarboxylic acid. Other prior art in this field supports the notion that ozonolysis is most selective at lower temperatures. All of the examples in the Maggiolo patent involve batch reactions in which the problems of continuous processes are not encountered. One of the more significant problems is that of limited solubility of cycloalkenes in organic solvents. If, in an ozonolysis reactor, cycloalkene were added to solvent in excess of the solubility limit, the cycloalkene/solvent mixture would separate into two liquid phases: one consisting of pure cycloalkene, and the other comprising cycloalkene, solvent and ozonide. The separation would result in a reduction in ozonide yield due to the formation of unwanted byproducts in the pure cycloalkene phase. If, however, the cycloalkene were kept at the solubility limit, the molar concentration of ozonide would be expected to be the same as that of the cycloalkene.

It would be desirable to have a continuous process for converting cycloalkenes into their corresponding $\alpha, \omega$ dicarboxylic acids. In such a continuous process, the solvent and cycloalkene would be fed continuously to an ozonolysis reactor. Since the heat of reaction between ozone and cycloalkene is known to be very high, on the order of 100 kcal/gmole, a large amount of heat would have to be conducted away from the reactor to maintain an appropriate reaction temperature. Finally, as is known for continuous processes in general, the higher the loading of reactants, the higher the efficiency and yield.

SUMMARY OF THE INVENTION

The present invention is directed specifically to the ozonolysis step of a continuous process for converting a cycyloalkene into its corresponding ozonide. Ultimately, the ozonide may be oxidized to obtain an $\alpha, \omega$ dicarboxylic acid, as in U.S. Pat. No. 3,280,183. Alternatively, the ozonide may be efficiently rearranged to make a product having both an aldehyde end group and an acid end group (aldehyde/acid). The aldehyde/acid can then be used, for example, as an intermediate for making cyclic lactones, cyclic lactams and a wide variety of other useful compounds.

Specifically, in its first aspect the present invention is a process for producing the ozonide of a C6 to C12 cycloalkene comprising:

contacting in a reaction vessel (1) a mixture of the cycloalkene and a solvent therefor with (2) a carrier gas containing about 1 to 2% ozone at a temperature of about 20 degrees, withdrawing from the reaction vessel a product stream comprising the carrier gas and a liquid comprising the ozonide dissolved in the solvent, separating the liquid from the gas, withdrawing heat from the liquid to form a cooled product stream, mixing a portion of the cooled product stream with additional cycloalkene to form a single, liquid phase cycloalkene-supplemented recycle stream, and adding the recycle stream to the reaction vessel.

In its second aspect the present invention is a process for producing the ozonide of a C6 to C12 cycloalkene comprising:

contacting in a cooled multistage distillation column (1) a mixture of the cylcoalkene and a solvent therefor with (2) a countercurrently flowing carrier gas containing about 1 to 2% ozone at a temperature of about 20 degrees C.;

withdrawing carrier gas from the reaction vessel;

withdrawing from the reaction vessel a liquid comprising the ozonide dissolved in the solvent;

returning to the reaction vessel a portion of the liquid while adding additional cycloalkene to the reaction vessel; and recovering a portion of the liquid as a product.

BRIEF DESCRIPTION OF THE DRAWING

The Drawing consists of two figures.

DETAILED DESCRIPTION OF THE INVENTION

Figure 1:
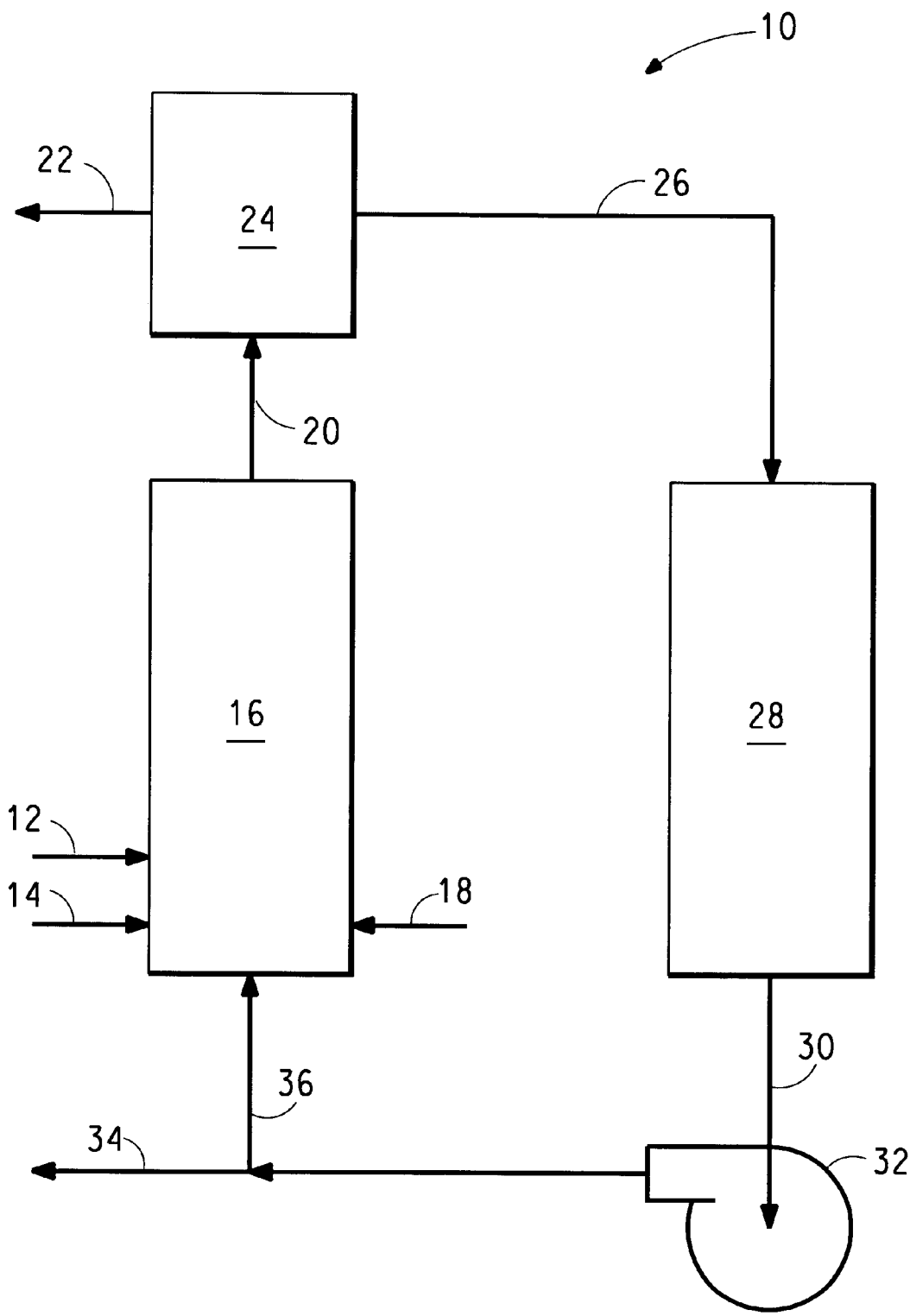
FIG. 1 depicts apparatus for use in the first aspect of the invention.

Referring now to FIG. 1, there is shown a loop ozonolysis apparatus 10 for practicing the process of the present invention. Cycloalkene 12 and solvent 14 are fed to an ozonolysis reactor 16. Suitable reactors include a continuously stirred tank reactor, static mixer located in a tubular reactor, a spray column reactor, a bubble column reactor, an Oldershaw column reactor, etc. Preferred cyclaolkenes are cyclododecane and cyclohexene, and their corresponding ozonides are cyclododecane molozonide and cyclohexane molozonide. A mixture 18 of ozone and carrier gas is also fed to the reactor 16. Suitable carrier gases include nitrogen, carbon dioxide, and Nobel gases. Within the reactor, a stoichiometric amount of ozone is reacted with cycloalkene to convert the cycloalkene completely to the corresponding ozonide (ozonolysis). Preferably the ozonolysis is carried out at 25° C. or lower to assure that a high ozonide yield is achieved. Following the ozonolysis, the remaining carrier gas 22 is separated from the product stream 20. This is typically done in a gas/liquid separator 24. Suitable gas/liquid separators include simply a tank, a tank with packing material, etc. The carrier gas 22 may be expelled from the process or recycled. Ozone can be added to the removed carrier gas and the resulting mixture fed once again to the ozonolysis reactor 16. A liquid 26 comprising the solvent and ozonide is then cooled in a heat exchanger 28. Suitable heat exchangers include a shell and tube heat exchanger, a vacuum chiller, etc. The purpose of the heat exchanger 28 is to remove all of the heat of the ozonolysis reaction and to return the liquid 26 to the original temperature. A cooled product stream 30 is then pumped back to the ozonolysis reactor 16, using pump 32. A portion of the cooled product stream 30 is removed after the pump 32 to become the desired ozonide product 34. The remaining cooled product stream 36, comprising solvent and ozonide, is sent through the reactor loop apparatus 10 another time.

Figure 2:
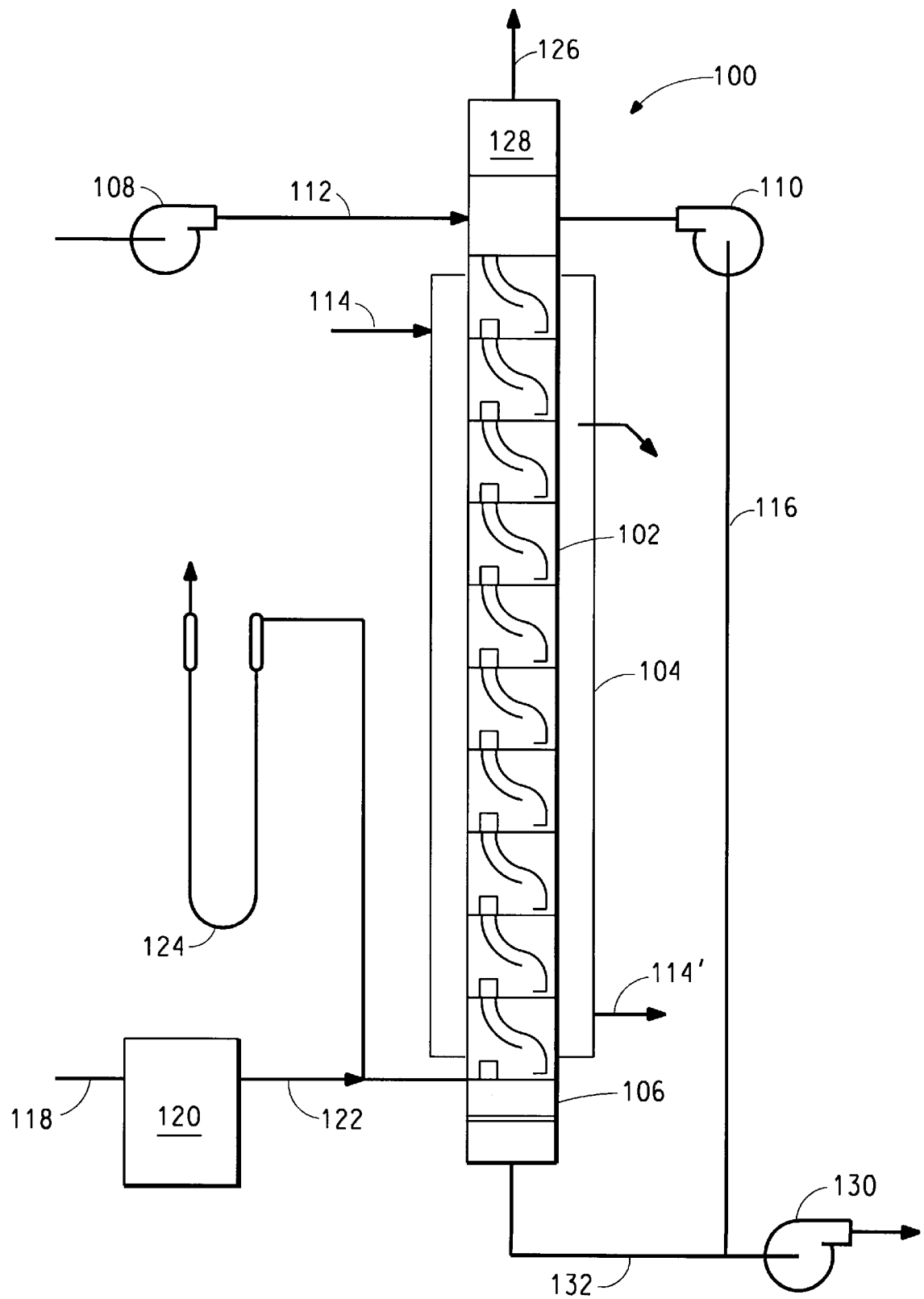
FIG. 2 depicts apparatus for use in the second aspect of the invention.

Referring now to FIG. 2, there is shown an alternative apparatus 100 for practicing the process of the present invention. The alternative apparatus for practicing the present invention includes a multistage distillation column, such as a multi-tray, glass Oldershaw column 102, enclosed in a cooling jacket 104. The apparatus also includes a bottom receiver 106, feed pump 108, and recycle pump 110. The initial feed material 112 consists of solvent and cycloalkene. Feed pump 108 charges the initial feed material 112 into the top of column 102. The temperature of the cooling jacket 104 on column 102 can be adjusted to between 0 and 25 degrees C. using flowing water 114, 114'. Recycle pump 110 can be used to establish a recycle flow 116 in column 102. A gas 118 consisting of a predetermined percentage of oxygen in carrier gas can be fed to ozone generator 120. The gas 122 exiting the ozone generator 120 can be measured to determine the percentage of ozone. This gas is fed to the bottom of column 102 in which it flows countercurrently to the flow of feed material 112. A pressure relief valve 124 can be used to control the pressure of gas 122. Additional cycloalkene solution can be fed to the top of the column 102 using feed pump 108. The balance between the ozone and the cycloalkene feed should allow for an excess of ozone in the reactor off-gas 126 at all times. The off-gas is formed by demister 128 located at the top of column 102. Pump 130 is used to pump the product solution 132 of ozonide in solvent to additional apparatus (not shown) or storage.

The inventory of material in the loop is maintained so as to allow the heat of reaction to be absorbed with only a few degrees of adiabatic heating. If ozone were reacted with cycloalkene and solvent in a single pass without the large loop inventory, the heat of reaction would cause the mixture to adiabatically heat to over 100° C. As taught by Maggiolo, this would not be desireable.

There are several advantages offered by the process of the present invention:

a. the present process is a continuous process;

b. the removal of the heat of reaction is adequately handled; and c. surprisingly high molar concentrations of ozonide in solvent are achieved.

Generally, cycloalkenes have a limited solubility in monocarboxylic acid solvents. For example, cyclododecene (C12) will dissolve only up to about 15% by weight in propionic acid. This might be expected to limit the ultimate loading of reactants in the process to 15%, with a limit on the resulting ozonide concentration. However, using cyclododecene in the present process, ozonide solubility in propionic acid has been found to be about 27.5%, surprisingly higher than that of the pure cyclododecene reactant.

EXAMPLE

A reactor system consisting of a jacketed 1 inch, 10 tray glass Oldershaw column, 250 cc bottom receiver, feed pump, and recycle pump were assembled. See FIG. II. The initial feed material consisted of 102 g. of propionic acid solvent and 18 g. of cyclododecene. 120 g. of the initial feed material were charged into the reactor system. The temperature of the jacket on the Oldershaw column was adjusted to 20° C. and a recycle flow of 50 cc/min. was established using the recycle pump. An ClearWater Tech modelM-1500 ozone generator was attached to the system. A carrier gas consisting of 20% oxygen in carbon dioxide was fed to the reactor at 2000 cc/min. The gas exit the ozone generator was measured to contain 0.80% ozone. After approximately 1 hour of feeding ozone, the ozone level was shown to increase as indicated by a gas bubbler containing aqueous potassium iodide. At that point, the additional 18 g. of pure CDDM solution was fed to the top of the column at a rate of 00.15 cc/min. The balance between the ozone and the cyclododecene fed allowed an excess of ozone in the reactor off gas at all times. When the additional feed material was depleted, the total loading of cyclododecene ozonide in the solution was over 27.5%. This affords a much higher loading of reactant in the succeeding stages of the process.

What is claimed:

1. A process for producing the ozonide of a C6 to C12 cycloalkene comprising:

contacting in a reaction vessel (1) a mixture of the cycloalkene and a solvent therefor with (2) a carrier gas containing about 1 to 2% ozone at a temperature of about 20 degrees, withdrawing from the reaction vessel a product stream comprising the carrier gas and a liquid comprising the ozonide dissolved in the solvent, separating the liquid from the gas, withdrawing heat from the liquid to form a cooled product stream, mixing a portion of the cooled product stream with additional cycoalkene to form a single, liquid phase cycloalkenesupplemented recycle stream, and adding the recycle stream to the reaction vessel.

2. A process for producing the ozonide of a C6 to C12 cycloalkene comprising:

contacting in a cooled multistage distillation column (1) a mixture of the cylcoalkene and a solvent therefor with (2) a countercurrently flowing carrier gas containing about 1 to 2% ozone at a temperature of about 20 degrees C.;

withdrawing carrier gas from the reaction vessel;

withdrawing from the reaction vessel a liquid comprising the ozonide dissolved in the solvent;

returning to the reaction vessel a portion of the liquid while adding additional cycloalkene to the reaction vessel; and recovering a portion of the liquid as a product.

* * * * *